US006194213B1

(12) United States Patent
Barbera-Guillem

(10) Patent No.: US 6,194,213 B1
(45) Date of Patent: Feb. 27, 2001

(54) LIPOPHILIC, FUNCTIONALIZED NANOCRYSTALS AND THEIR USE FOR FLUORESCENCE LABELING OF MEMBRANES

(75) Inventor: Emilio Barbera-Guillem, Powell, OH (US)

(73) Assignee: Bio-Pixels Ltd., Westerville, OH (US)

( * ) Notice: Subject to any disclaimer, the term of this patent is extended or adjusted under 35 U.S.C. 154(b) by 0 days.

(21) Appl. No.: 09/458,752

(22) Filed: Dec. 10, 1999

(51) Int. Cl.$^7$ .............................. G01N 33/53; C12Q 1/00; B32B 15/02

(52) U.S. Cl. ............................ 435/968; 435/7.2; 435/7.1; 435/4; 428/402.2

(58) Field of Search .............................. 435/968, 7.2, 7.1, 435/4; 428/402.2

(56) References Cited

U.S. PATENT DOCUMENTS 5,503,723 * 4/1996 Ruddy et al. ........................ 204/450
5,990,479 11/1999 Weiss et al. ......................... 250/307
6,114,038 * 9/2000 Castro et al. ........................ 428/402

OTHER PUBLICATIONS

Jacoby, "Quantum dots meet biomolecules", C&EN, 1998, Sep. 28, p. 8.

Emory et al., "Direct observation of size–dependent optical enhancement in single metal nanoparticles", 1998, J. Am. Chem. Soc., vol. 12: 8009–8010.

Chan and Nie, "Quantum dot bioconjugates for ultrasensitive nonisotopic detection", Science, vol. 281: 2016–2018.

Service, "Semiconductor beacons light up cell structures", Science, 1998, Sep. 25, vol. 281:1930–1931.

Bruchez et al., "Semiconductor nanocrystals as fluorescent biological labels", Science, 1998, Sep. 25, vol. 281:2013–2015.

* cited by examiner

*Primary Examiner*—Louise N. Leary
(74) *Attorney, Agent, or Firm*—M Bud Nelson

(57) ABSTRACT

Provided is a method of fluorescence detection of lipid membranes using lipophilic, functionalized nanocrystals; and lipid membranes labeled by the lipophilic, functionalized nanocrystals. The method comprises contacting an effective amount of lipophilic, functionalized nanocrystals with the lipid membranes; exposing the labeled lipid membranes to an excitation light suitable for exciting the functionalized nanocrystals present in the labeled lipid membranes to emit a fluorescence emission. Also provided is a composition comprising a functionalized nanocrystal which is bound to a substrate in a living tissue.

21 Claims, 1 Drawing Sheet

LIPOPHILIC, FUNCTIONALIZED NANOCRYSTALS AND THEIR USE FOR FLUORESCENCE LABELING OF MEMBRANES

FIELD OF INVENTION

This invention relates to the field of detection of lipid membranes; and more particularly to functionalized nanocrystals which may be used to contact and incorporate into lipid-containing membranes in fluorescently labeling the membranes.

BACKGROUND OF THE INVENTION

Fluorescent dyes have a wide variety of uses including the labeling of proteins (e.g., antibodies), DNA, carbohydrates, and cells. Fluorescent-labeled substrates have been used for visualization and/or quantitative measurements in various applications including biology, medicine, electronics, biomedicine, and forensics. Typically, conventional fluorescent dyes are used to study biochemical, pharmacological, or pathological changes that occur in tissue by labeling various cell components. Examples of conventional fluorescent dyes which are used to detect cell components comprising lipid membranes include osmium tetraoxide, octadecyl rhodamine B, 2-hydroxyethyl-7,12,17-tris(methoxyethyl) porphycene, and 1,6-diphenyl-1,3,5-hexatriene. However, typically fluorescent dyes have characteristics which interfere with their usefulness. For example, many fluorescent dyes presently used do not have significant absorbance at the desired excitation wave-lengths, or are unstable in aqueous solutions, or are unstable during illumination. More specifically, conventional fluorescent dyes generally suffer from short-lived fluorescence; e.g., undergo photobleaching after minutes of exposure to an excitation light source. Thus, they are not very suitable for applications which requiring a significant length of time needed for ascertaining a staining pattern. Further, conventional fluorescent dyes are sensitive to changes in environment which can decrease their quantum yield. Another disadvantage of conventional fluorescent dyes is that typically the excitation spectrum of a species of fluorescent dye may be quite narrow. However, even when a single light source is used to provide excitation wavelength spectrum, in view of the spectral line width there often is insufficient spectral spacing between the emission optima of different species of fluorescent dyes to permit individual and quantitative detection without substantial spectral overlap. Thus, when using a combination of different fluorescent dyes as labels, multiple filters are typically needed to detect the resultant emission spectra of the combination. Conventional fluorescent dyes are limited in sensitivity and resolution of imaging due to the limitations of intensity, photobleaching, and the finite number of molecules which can be used to label a substrate.

Semiconductor nanocrystals ("quantum dots") are known in the art. Generally, quantum dots can be prepared which result in relative monodispersity; e.g., the diameter of the core varying approximately less than 10% between quantum dots in the preparation. Examples of quantum dots are known in the art to have a core selected from the group consisting of Group II–VI semiconductor materials, or Group III–V semiconductor materials. Preferred, illustrative examples include CdSe, CdS, or CdTe (collectively referred to as "CdX"). Quantum dots have been passivated with an inorganic coating ("shell") uniformly deposited thereon. Passivating the surface of the core quantum dot can result in an increase in the quantum yield of the fluorescence emission, depending on the nature of the inorganic coating. The shell which is used to passivate the quantum dot is preferably comprised of YZ wherein Y is Cd or Zn, and Z is S, or Se. Generally, quantum dots (core or core passivated with a shell) have only been soluble in organic, non-polar (or weakly polar) solvents. Thus, the instability of these quantum dots in aqueous media has limited their usefulness in biological applications.

To make quantum dots useful in applications for detection, it is desirable that the quantum dots are water-soluble. "Water-soluble" is used herein to mean sufficiently soluble or suspendable in a aqueous-based solution, such as in water or water-based solutions or physiological solutions, including those used in biological or molecular detection systems as known by those skilled in the art. Several attempts have been made to impart water solubility to nanocrystals such as by treating the water-insoluble quantum dots with a large excess of mercaptocarboxylic acid in $CHCl_3$ solution (Chan and Nie, 1998, Science 281:2016–2018), or by silicanizing the surface of quantum dots (U.S. Pat. No. 5,990,479). However, depending on the nature of the coating group, quantum dots which have been reported as water-soluble may have limited stability in an aqueous solution, particularly when exposed to air (oxygen) and/or light. More particularly, oxygen and light can cause the molecules comprising the coating to become oxidized, thereby forming disulfides which destabilize the attachment of the coating molecules to the shell. Thus, oxidation may cause the coating molecules to migrate away from the surface of the quantum dots, thereby exposing the surface of the quantum dots in resulting in "destabilized quantum dots". Destabilized quantum dots form aggregates when they interact together, and the formation of such aggregates eventually leads to irreversible flocculation of the nanocrystals. Additionally, such treated quantum dots are not lipophilic.

Thus, current fluorescent molecules (fluorescent dyes and quantum dots) have characteristics which can limit their usefulness in labeling lipid membranes. In that regard, provided herein are fluorescent molecules that are: (a) functionalized to enhance stability in aqueous environments; (b) functionalized to be lipophilic; (c) extremely sensitive in terms of detection, because of their fluorescent properties (e.g., including, but not limited to, high quantum efficiency, resistance to photobleaching, and stability in complex aqueous environments); and (d) a class of semiconductor nanocrystals that may be excited with a single wavelength of light resulting in detectable fluorescence emissions of high quantum yield and with discrete fluorescence peaks.

SUMMARY OF THE INVENTION

The present invention provides a method for fluorescence labeling of lipid-containing membranes (for purposes of brevity, "lipid membranes") by contacting the membranes desired to be labeled with an effective amount of nanocrystals functionalized to be lipophilic. The present invention provides a method for fluorescence detection of lipid membranes by contacting the membranes desired to be detected with an effective amount of lipophilic functionalized nanocrystals in labeling the membranes, exposing the labeled membranes to a excitation light source, and then detecting (one or more of visualizing, imaging, measuring, and quantitating) the fluorescence emitted from the excited functionalized nanocrystals in the labeled membranes. The functionalized nanocrystals comprise quantum dots capped with a polar capping compound (multiple molecules of capping compound also referred herein, for ease of reference, as a layer of capping compound), and molecules of an amino acid (diaminocarboxylic acid or monoaminocarboxylic acid) which are operatively linked to the layer of polar capping compound (multiple amino acid molecules also referred to herein for ease of reference as a layer of amino acid). The functionalized nanocrystals may further comprise one or more operatively linked successive amino acid layers operatively linked to the first layer of amino acid.

In a method of fluorescence detection of lipid membranes using functionalized nanocrystals, an effective amount of functionalized nanocrystals may be mixed with a suitable physiologically acceptable carrier (e.g., an aqueous solution); the resultant mixture is then placed in contact with substrate comprising the lipid membranes to be labeled; the labeled membranes are then exposed to a light source comprising an excitation spectrum in the range of from about 190 nanometers (nm) to about 660 nm (the highest functional wavelength for excitation may depend on the wavelength of the maximum peak of the emission spectrum for the color of the lowest wavelength to be detected; e.g., the highest wavelength of the excitation spectrum should not be greater than the lowest wavelength of the emission spectrum sought to be detected); and detected is any emission peak having a narrow spectral band (e.g. between about 10 nm to about 60 nm), and comprising an emission spectrum in the range of from about 400 nm to about 750 nm, wherein any such emission peak detected comprises a detectable signal emitted by the excited functionalized nanocrystals in the labeled lipid membranes.

Another object of the present invention is to provide a composition comprising fluorescently labeled lipid membranes comprising lipid membranes having incorporated therein, or associated therewith, lipophilic, functionalized nanocrystals.

The above and other objects, features, and advantages of the present invention will be apparent in the following Detailed Description of the Invention when read in conjunction with the accompanying drawings.

DETAILED DESCRIPTION OF THE INVENTION

Definitions

Figure 1:
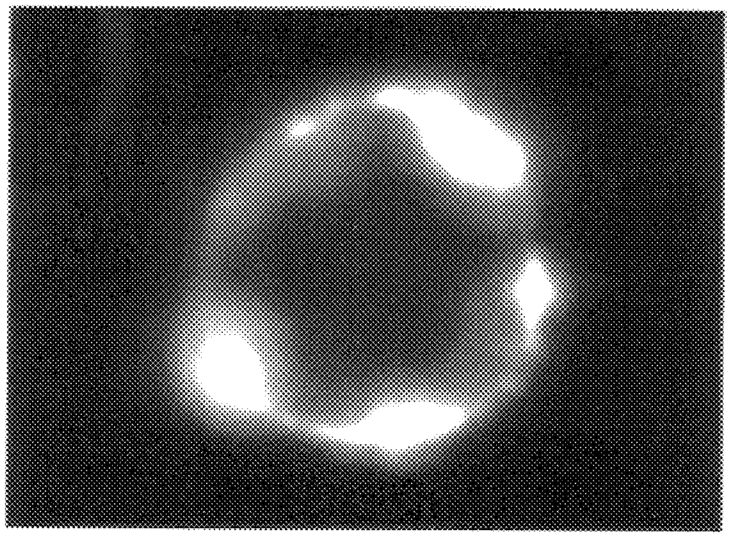
FIG. 1 a black and white representation of a photographic image showing a Jurkat cell labeled with an effective amount of lipophilic, functionalized nanocrystals.

By the terms "lipid-containing membrane" and "lipid membrane" is meant, for the purposes of the specification and claims to refer to a membrane which is comprised, at least in part, of lipid; and may further comprise lipid membranes comprising a substrate. The lipid membrane may be selected from the group consisting of a monolayer, bilayer, or multi-layer. Lipid membranes are known to those skilled in the art to include cell membranes (e.g., lipid bilayer containing other molecules such as proteins), liposomes, and lipid membrane-coated biosensors. Regarding cell membranes, lipid membranes may comprise a substrate comprising intact cells, isolated cells, a preparation comprising cell membranes isolated from cells, and a tissue (e.g., tissue section) containing cell membranes to be labeled. Regarding lipid membrane-coated biosensors, methods for assembling lipid membranes (not derived from cell membranes) or cell membranes onto a substrate in forming a biosensor are known in the art (see, e.g., U.S. Pat. Nos. 4,931,498, and 5,919,576). Regarding liposomes, methods for making liposomes are well known in the art (see, e.g., U.S. Pat. Nos. 4,529,561, 4,687,661, 4,744,989, 4,877,561, 5,000,959, 5,080,904, and 5,540,936). Typically, liposomes are prepared using a two-phase mixing process, wherein lipid or a mixture of lipids is dissolved in an organic solvent, and then added to an aqueous phase containing a dissolved salt or buffer (and may further comprise a substance such as a drug or bioactive agent to be loaded in the liposomes). A preferred lipid membrane may be used to the exclusion of a lipid membrane other than the preferred lipid membrane.

By the term "operably linked" is meant, for purposes of the specification and claims to refer to fusion or bond or an association of sufficient stability to withstand conditions encountered in a method of detection, between a combination of different molecules such as, but not limited to, between the quantum dot and a capping compound, between a capping compound and an amino acid, between an amino acid and an amino acid, and a combination thereof. As known to those skilled in the art, and as will be more apparent by the following embodiments, there are several methods and compositions in which two or more molecules may be operably linked utilizing reactive functionalities such as free chemical groups (e.g., thiol, or carboxyl, hydroxyl, amino, amine, sulfo, etc.), and reactive chemical groups (reactive with free chemical groups).

By the term "diaminocarboxylic acid" is meant, for purposes of the specification and claims to refer to an amino acid that has two free amine groups, and contains one or more free chemical groups. The amino acid may be a naturally occurring amino acid, a synthetic amino acid, a modified amino acid, an amino acid derivative, an amino acid precursor (e.g., citrulline and ornithine are intermediates in the synthesis of arginine), or a combination thereof. In a preferred embodiment, the diaminocarboxylic acid contains free chemical groups which comprise neutral (uncharged) polar functional groups which can hydrogen bond with water, thereby making the diaminocarboxylic acid (and the quantum dot to which it is made a part of) relatively more soluble in aqueous solutions containing water than those with nonpolar functional groups. Exemplary diaminocarboxylic acids include, but are not limited to, lysine, asparagine, glutamine, arginine, citrulline, ornithine, 5-hydroxylysine, djenkolic acid, β-cyanoalanine, a synthetic diaminocarboxylic acid (e.g., such as 3,4-diamino-benzoic acid, 2,3-diaminopropionic acid, 2,4-diaminobutyric acid, 2,5-diaminopentanoic acid, 2,6-diaminopimelic acid), and a combination thereof. A preferred diaminocarboxylic acid may be used to the exclusion of a diaminocarboxylic acid other than the preferred diaminocarboxylic acid.

By the term "amino acid" is meant, for purposes of the specification and claims to refer to a molecule that has contains one or more free chemical reactive groups, and in a preferred embodiment, has at least one free amine group and at least one free carboxyl group. The amino acid may have more than one free amine group, or more than one free carboxyl group, or may further comprise one or more free chemical reactive groups other than an amine or a carboxyl group (e.g., a hydroxyl, a sulfhydryl, etc.). The amino acid may be a naturally occurring amino acid, a synthetic amino acid, a modified amino acid, an amino acid derivative, and an amino acid precursor. The amino acid may further be selected from the group consisting of a monoaminocarboxylic acid, and a diaminocarboxylic acid. In a preferred embodiment, the monoaminocarboxylic acid contains one or more neutral (uncharged) polar functional groups which can hydrogen bond with water, thereby making the monoaminocarboxylic acid (and the quantum dot to which it is made a part of) relatively more soluble in aqueous solutions containing water than those with non-polar functional groups. Exemplary monoaminocarboxylic acids include, but are not limited to, glycine, serine, threonine, cysteine, β-alanine, homoserine, γ-aminobutyric acid, homocysteine, and a combination thereof. A preferred amino acid may be used to the exclusion of an amino acid other than the preferred amino acid.

By the term "capping compound" is meant, for purposes of the specification and claims to refer to a compound having the formula $HS(CH_2)_nX$, wherein X is a carboxylate (carboxylic moiety); or the formula $HS(CH_2)_nYX$, wherein X is a carboxylate and Y is an amine, as will be more apparent from the following descriptions. "n" is a number in the range of from 1 to about 20, and preferably greater than 4. The thiol group of the capping compound may form sulfide bonds with a quantum dot comprised of semiconductor materials having a chemical functionality reactive with a free sulfur containing group. Additionally, the carboxylic acid moiety of the capping compound imparts some water solubility to the quantum dots. Exemplary capping compounds include, but are not limited to, mercaptocarboxylic acid, or mercaptofunctionalized amines (e.g., aminoethanethiol-HCl, homocysteine, or 1-amino-2-methyl-2-propanethiol-HCl), or a combination thereof. A preferred capping compound may be used to the exclusion of a capping compound other than the preferred capping compound.

By the terms "lipophilic, functionalized nanocrystals" and "functionalized nanocrystals" are meant, for purposes of the specification and claims, to refer to nanocrystals comprised of (in order of arrangement): quantum dots, a capping compound, and amino acid, as will be more apparent from the descriptions herein. In a preferred embodiment the amino acid comprises a layer of diaminocarboxylic acid containing neutral (uncharged) polar functional groups which can hydrogen bond with water. A preferred functionalized nanocrystal may be used to the exclusion of a functionalized nanocrystals other than the preferred functionalized nanocrystal.

By the term "quantum dots" is meant, for purposes of the specification and claims to refer to semiconductor nanocrystals (e.g., crystalline semiconductors) comprised of a core comprised of at least one of a Group II–VI semiconductor material (of which ZnS, and CdSe are illustrative examples), or a Group III–V semiconductor material (of which GaAs is an illustrative example), or a combination thereof. In an additional embodiment, the semiconductor nanocrystal may further comprise a selected dopant (e.g., with a fluorescense property) such as a rare earth metal or a transition metal, as known to those skilled in the art. In a preferred embodiment, and as selected from the aforementioned semiconductor materials, the semiconductor nanocrystal comprises a metal cation and an anion (e.g., the anion comprising a chalcogenide when forming a Group II–VI material, or comprising a pnictide when forming a Group III–V material). In another preferred embodiment, the quantum dot further comprises a shell which passivates the core. As an illustrative example, a core of CdX (wherein X is Se or Te or S) is passivated with a shell preferably comprised of YZ (wherein Y is Cd or Zn, and Z is S, or Se), and then operably linked to a capping compound, followed by operably linking amino acid to the capping compound. Preferred quantum dots may be used to the exclusion of quantum dots other than the preferred quantum dots.

By the term "effective amount" is meant, when used in conjunction with functionalized nanocrystals and for purposes of the specification and claims, to refer to an amount of functionalized nanocrystals sufficient to contact lipid membrane to be fluorescence labeled; and an amount which, when excited with an appropriate excitation light source, will emit fluorescence emission sufficient for detecting the fluorescently labeled lipid membrane when using an appropriate detection means. As apparent to one skilled in the art, such an amount will vary depending on factors which include, but are not limited to, the amount of lipid membranes to be detected, the rate of incorporation of the functionalized nanocrystals into contacted lipid membranes to be labeled, the method used in preparing the lipid membranes for labeling, the method and reagents used for the labeling process, and the system used to detect the fluorescently labeled lipid membranes.

The present invention provides for lipophilic, functionalized nanocrystals that, when in contact with lipid membranes, may be incorporated into the membranes in a method of fluorescence labeling of the lipid membranes. While it will be apparent to one skilled in the art that the method according to the present invention, and resultant labeled lipid membranes, have many different utilities, preferred uses of the present invention include: providing a new histological tool for detecting changes in morphology of cells due to a disease process; providing a tool for labeling cell membranes that may be used in conjunction with labeling of cell components other than lipid membranes such as in histological or flow cytometric analyses for detecting and/or discriminating between cell populations in a sample comprising multiple populations of cells (e.g., it has been reported that membrane lipid composition can vary between different human T lymphocyte subpopulations); and providing a new tool for tracking loaded liposomes (e.g., such as tracking drug delivery of loaded liposomes by identifying where such liposomes localize in a tissue). In such uses, the lipid membranes of the substrate (e.g., tissue, cells, or liposomes) are contacted with, and incorporate, the lipophilic, functionalized nanocrystals. It was discovered that these functionalized nanocrystals have a propensity to be inserted into a membrane, particularly a membrane comprising a bilayer of lipids (e.g., a membrane comprising a fluid phospholipid bilayer), in associating with lipids in the membrane. While not intending to be bound by theory, it is believed that the unique structure and features of the functionalized nanocrystals, substantially comprising polar entities in spatial relation to hydrocarbon chains and hydrophobic entities, contribute to the functionalized nanocrystals being incorporated into a lipid membrane in an orientation and manner similar to that of phospholipids; i.e., the hydrophilic portion (e.g., free polar chemical reactive groups or "head") of the amino acid is orientated outward, whereas the hydrocarbon chains are oriented inward in forming a hydrophobic phase. Similarly, in a lipid membrane comprising a monolayer, above the critical micelle concentration, the hydrocarbon portion may be hidden from the aqueous environment, whereas the hydrophilic heads may be exposed to the aqueous interface in forming micelles.

The lipophilic, functionalized nanocrystals: may be excited with a single excitation light source; when excited, result in a detectable light emission (e.g., fluorescence emission) of high quantum yield (e.g., a single quantum dot having at a fluorescence intensity greater than that of at least 10 rhodamine molecules); emit a light emission having a discrete fluorescence peak; are water-soluble; are lipophilic such that they can be used, by themselves (e.g., without using a linker) to label lipid membranes. Also, as related to the method of labeling lipid membranes and in a method of fluorescence detection of lipid membranes, in a preferred embodiment according to the present invention, the functionalized nanocrystals typically should have a substantially uniform size (monodisperse) in the range of sizes of from about 15 nm to about 30 nm (diameter); and in a more preferred embodiment, a size in the range of from about 18 nm to about 24 nm. Preferred quantum dots used in the production of functionalized nanocrystals are comprised of a core of CdX wherein X is Se or Te or S. Such CdX quantum dots are passivated with an over-layering ("shell") uniformly deposited thereon, wherein the shell is preferably comprised of YZ wherein Y is Cd or Zn, and Z is S, or Se. It is noted that, although the following examples emphasize the use of quantum dots comprising a CdSe core, the method of the present invention is general and can be applied using other Group II–VI semiconductor nanocrystals, or Group III–V semiconductor nanocrystals, as will be apparent to those skilled in the art from the descriptions herein. More particularly, using methods known in the art for producing a semiconductor nanocrystal of a desired composition, size, and monodispersity, such quantum dots can be functionalized to include a capping compound and amino acid in optimum combinations thereof as determined by the descriptions herein and through ordinary experimentation to maximize the yield and desired characteristics of the resultant lipophilic, functionalized nanocrystals produced.

EXAMPLE 1

In this embodiment is illustrated the production of functionalized nanocrystals. Various methods for producing Group II–VI quantum dots and for producing Group III–V quantum dots are known in the art. Exemplary quantum dots comprise a CdSe core, and a ZnS shell, "(CdSe)ZnS". TOPO capped CdSe were produced by placing TOPO (5 g) in a vessel, and dried at 150° C. for 1 hour under vacuum. The vessel was then backfilled with argon and heated to 300° C. In a controlled environment, $CdMe_2$ (7.2 $\mu$l , 0.1 mmol) and 1 M trioctylphosphine-Se solution (90 $\mu$l , 0.09 mmol) and trioctylphosphine (5 ml) were mixed, and then placed into an injector. This mixture was added to the TOPO in a reaction vessel, previously removed from the heat, in a single continuous injection with vigorous stirring, thereby resulting in the temperature decreasing to about 180° C. The reaction vessel was then subjected to heat to raise the temperature 5° C. every 10 minutes. Aliquots may be removed from the reaction vessel at various time intervals (5 to 10 minutes) to monitor the increase in size of quantum dots over time, by the observation of the absorption spectra. The temperature may be changed, or the reaction halted, upon reaching quantum dots of the desired characteristics. For example, the reaction vessel was cooled to about 60° C., 40 ml of methanol was added to cause the quantum dots to flocculate. After centrifugation, a brightly colored liquid layer of quantum dots dissolved in trioctylphosphine remained. The methanol/TOPO layer was decanted off, pyridine (10 ml) was added to the solution of quantum dots, and the solution was allowed to stand for at least one hour. The quantum dots were then precipitated as a powder by addition of hexanes, and separated by centrifugation. The powder was washed once more with hexanes, then dissolved in 30 ml pyridine, and centrifuged to remove any reaction byproducts.

To prepare (CdSe)ZnS quantum dots, the pyridine solution (30 ml) was placed in a reaction vessel, rigorously degassed with an inert gas (e.g., argon), and refluxed for one hour before adjusting the temperature to approximately 100° C. Equimolar amounts of diethyl zinc (zinc source) and hexamethyldisilathiane (sulfide source) were dissolved in trioctylphosphine (2–4 ml) in a controlled environment (glove box) and loaded into an injector. A reaction vessel containing the CdSe dots dispersed in pyridine was heated under an atmosphere of argon, and the Zn and S were added dropwise, via the injector, with vigorous stirring of the mixture for 5–10 minutes. The mixture was left stirring for several hours. After cooling, the pyridine solution was centrifuged to remove any insoluble material. The overcoated quantum dots were stored in this solution to ensure that the surface of the quantum dots remained passivated with pyridine.

To prepare nanocrystals which have some water solubility, the pyridine overcoating of the (CdX) core/YZ shell quantum dots were exchanged with a capping compound which contributes to the water-solubility of the resultant nanocrystals. For example, a capping compound comprising mercaptocarboxylic acid may be used to exchange with the pyridine overcoat. Exchange of the coating group is accomplished by treating the water-insoluble, pyridine-capped quantum dots with a large excess of neat mercaptocarboxylic acid. To accomplish this, the pyridine-capped (CdSe)ZnS quantum dots were precipitated with hexanes, and then isolated by centrifugation. The residue was dissolved in neat mercaptoacetic acid, with a few drops of pyridine added, if necessary, to form a transparent solution. The solution is allowed to stand at room temperature for at least six hours. Longer incubation times lead to increased substitution by the thiol. Overnight incubations are ideal. Chloroform is added to precipitate the nanocrystals and wash away excess thiol. The nanocrystals were isolated by centrifugation, washed once more with chloroform, and then washed with hexanes. The residue was briefly dried with a stream of argon. The resultant nanocrystals, coated with the capping compound, were then soluble in water or other aqueous solutions. The nanocrystals, in an aqueous solution, were centrifuged once more, filtered through a 0.2 $\mu$m filter, degassed with argon, and stored in an amber vial. Failure to protect the nanocrystals, in solution, from air and light leads to irreversible flocculation, usually within a week. Although proper storage conditions can extend the shelf life of these water-soluble nanocrystals to several months, there is a drawback because of their sensitivity to oxidation, and a need for repeatedly degassing the vial after each use. As mentioned previously, oxidation may result in the capping compound becoming destabilized (e.g., individual molecules of the capping compound form disulfides, and lose contact with the shell of the nanocrystal); and destabilization can result in irreversible flocculation of the nanocrystals.

The nanocrystals, capped with the capping compound, were then overlayered with an organic molecule comprising amino acid in forming functionalized nanocrystals. In a preferred embodiment, the amino acid contributes to the water-solubility of the functionalized nanocrystal because it has polar functional groups which can hydrogenbond with water, and contributes to the overall ability of the functionalized nanocrystal to be incorporated as a unit into a lipid membrane with which it is contacted. In a preferred embodiment, the amino acid comprises a diaminocarboxylic acid which has at least two free functional groups which are carboxyl-reactive, thereby enabling the diaminocarboxylic acid molecule to operably link to and crosslink carboxyl groups extending from the capping compound on the nanocrystal in contributing to stability of the resultant structure. If desired, one or more additional, successive layers of amino acid may be added which may further protect the capping compound from oxidation by light and/or air.

For operably linking amino acid to the capping compound of capped nanocrystals, commercially available crosslinking agents and methods known to those skilled in the art may be used. For example, mercaptoacetic acidcapped nanocrystals were dissolved in an aqueous buffer system (pH of about 7). The buffer may comprise such buffers as PBS or HEPES. It is noted that the presence of phosphate may affect the crosslinking agent. To the capped nanocrystals was added EDC (1-ethyl-3-[3-dimethylaminopropyl] carbdiimide) and sulfoNHS (sulfo-N-hydroxysuccinimide) in 500–1000 times excess. The resulting solution was stirred at room temperature for 30 minutes. Mercaptoethanol was added to neutralize unreacted EDC at 20 mM concentration and stirred for 15 minutes. The entire solution was then added dropwise, with stirring, to a solution of amino acid (large excess) in the same buffer; and the mixture was stirred for 2 hours at room temperature. Ethanolamine (30 mM) was added to quench the reaction; and the mixture was stirred for 30 minutes at room temperature or left overnight at 4° C. The solution was centrifuged to remove any precipitated solids, and then ultrafiltered through a 30 kD MW centrifugal filter. The resultant concentrated, functionalized nanocrystals can be solubilized in an aqueous solution of choice. Once solubilized, the resulting solution can be stored in an amber vial under an inert gas to prevent flocculation. In a preferred embodiment, the amino acid comprises a diaminocarboxylic acid; and in a more preferred embodiment, the diaminocarboxylic acid comprises lysine.

In another embodiment, the functionalized nanocrystals, comprised of an outermost layer comprising amino acid, may be further functionalized by the addition of one or more successive layers of amino acid using methodology similar to that used for operably linking the first layer of amino acid to the nanocrystals. For example, the amino acid molecules of each additional layer can operably link, and crosslink, the free chemical reactive groups (e.g., carboxyl groups) on the amino acid molecules comprising the preceding layer. In one illustrative embodiment, functionalized nanocrystals, comprising an outermost layer of amino acid comprising diaminocarboxylic acid, are mixed with EDC and sulfo-NHS in 500–1000 times excess. The resulting solution is stirred at room temperature for 30 minutes. Mercaptoethanol is added to neutralize unreacted EDC at 20 mM concentration and stirred for 15 minutes. The entire solution is then added dropwise, with stirring, to a solution of a large excess of amino acid in the same buffer; and the mixture is stirred for 2 hours at room temperature. Ethanolamine (30 mM) is added to quench the reaction; and the mixture is stirred for 30 minutes at room temperature or left overnight at 4° C. The solution is centrifuged to remove and precipitate solids, and then ultrafiltered through a 30 kD MW centrifugal filter. The resultant concentrated, functionalized nanocrystals can be solubilized in an aqueous solution of choice. Once solubilized, the resulting solution can be stored in an amber vial under an inert gas to prevent flocculation. This process can be repeated to add one or more additional, successive layers comprising an amino acid. In a preferred embodiment, the amino acid comprises a diaminocarboxylic acid; and in a more preferred embodiment, the diaminocarboxylic acid comprises lysine.

EXAMPLE 2

In a method for fluorescence detection of lipid membranes according to the present invention, the lipid membranes are contacted with an effective amount of functionalized nanocrystals in fluorescent labeling the lipid membrane; the labeled membranes are then exposed to an excitation light source; and then detected is the fluorescence emission (one or more fluorescence peaks, depending if one or more than one species of lipophilic, functionalized nanocrystals are used) emitted from excited functionalized nanocrystals in the labeled membranes. In one illustrative embodiment of the method of fluorescence labeling of lipid membranes, an effective amount of functionalized nanocrystals may first be mixed with a suitable physiologically acceptable carrier. Physiologically acceptable carriers are known to those skilled in the art to include, but are not limited to, an aqueous solution, buffered solution, water, saline, phosphate buffered saline (PBS), tissue culture medium, and the like. The mixture comprising the functionalized nanocrystals and the suitable physiologically acceptable carrier may comprise a form such as a suspension or a solution or other suitable formulation for the intended purpose. The resultant mixture is then placed in contact with the lipid membranes to be labeled in labeling the lipid membranes. The labeled lipid membranes may then be exposed to a light source comprising an excitation spectrum in the range of from about 190 nm to about 660 nm (the highest functional wavelength for excitation depends on the wavelength of the maximum peak of the emission spectrum for the color of the lowest wavelength to be detected; e.g., the highest excitation wavelength should not exceed the lowest emission wavelength sought to be detected); and detected is any emission peak having a narrow spectral band (e.g., between about 10 nm to about 60 nm), and comprising an emission spectrum in the range of from about 400 nm to about 750 nm (the lowest emission wavelength detectable may depend on the excitation spectrum; e.g., the highest excitation wavelength should not exceed the lowest emission wavelength sought to be detected), wherein such an emission peak detected comprises a signal by which the labeled lipid membranes can be detected.

It will be apparent to one skilled in the art that multiple species of functionalized nanocrystals may be used in multicolor labeling and detection. For example, multicolor labeling may comprise multicolor labeling of lipid membranes, or may comprise fluorescence labeling of lipid membranes with lipophilic, functionalized nanocrystals and fluorescence labeling of cell components other than lipid membranes with fluorescent molecules or semiconductor nanocrystals functionalized with an affinity ligand bound thereto. Each of the species of functionalized nanocrystals may vary in color (e.g., because of core size or doping agent) as compared to other species of functionalized nanocrystals used in combination for multicolor labeling. For example, it will be apparent to those skilled in the art that more than one uniform size of functionalized nanocrystals may be used simultaneously in multicolor labeling. Thus, in one embodiment, multicolor labeling of lipid membranes may be performed. In a preferred embodiment wherein multicolor labeling and detection is performed, the light source suitable for exciting the multiple species of functionalized nanocrystals may comprise a spectrum (visible, or UV, or a combination thereof) that is suitable for exciting all of the species of functionalized nanocrystals used in the labeling step to emit a respective fluorescence peak. A preferred excitation spectrum for this purpose, and for the method according to the present invention, is in the range of about 300 nm to about 400 nm; and in a more preferred embodiment, from about 360 nm to about 365 nm.

Any fluorescence peak emitted by the excited functionalized nanocrystals present in the labeled lipid membranes is then detected by appropriate detection means or system (e.g., one or more of: photodetector, filter, charge couple device camera (CCD camera) fluorescence microscope, endoscopic imaging system, endoscopic fluorescence imaging microscope, a fiber optic fluorescence imaging microscope, a fluorescence cube, a computer for digitalizing a fluorescence image, and the like). In a preferred embodiment, the appropriate detection means can detect fluorescence peaks in the spectral range of about 400 nm to about 750 nm; and, when more than one color is used to label the tissue, distinguish between discrete fluorescence peaks within that range. Quantitation of the amount of labeled lipid membranes present is directly related to the intensity of an emitted fluorescence peak (e.g., the amount of functionalized nanocrystals incorporated therein). As known to those skilled in the art of nanocrystals, the absorbance peak and fluorescence peak emissions depend on properties of the nanocrystals which may include, but are not limited to, the chemical nature, doping agent (if any), and core size. The following are illustrative examples of altering the size of the core of the nanocrystal to achieve various colors. Functionalized CdSe/ZnS nanocrystals having a substantially uniform size comprising a diameter of about 68.4 angstroms (A) may be excited with light of a spectrum ranging from about 300 nm to about 400 nm, and emit a fluorescence peak (orange) at 609 nm which may be detected using appropriate detection means. Functionalized CdSe/ZnS nanocrystals having a substantially uniform size comprising a diameter of about 53.2 A may be excited with light of a spectrum ranging from about 300 nm to about 400 nm, and emit a fluorescence peak (yellow) at 545 nm which may be detected using appropriate detection means. Functionalized CdSe/ZnS nanocrystals having a substantially uniform size comprising a diameter of about 46.6 A may be excited with light of a spectrum ranging from about 300 nm to about 400 nm, and emit a fluorescence peak (green) at 522 nm which may be detected using appropriate detection means. Functionalized CdSe/ZnS nanocrystals having a substantially uniform size comprising a diameter of about 23 A may be excited with light of a spectrum ranging from about 300 nm to about 400 nm, and emit a fluorescence peak (blue) at 480 nm which may be detected using appropriate detection means. In a preferred embodiment, the size of the functionalized nanocrystals used in the labeling of lipid membranes according to the present invention is a size in the range of sizes that corresponds to a fluorescence peak which may be visualized as a color selected from the group consisting of yellow, orange, red, and a combination thereof.

EXAMPLE 3

In one illustrative embodiment of a method according to the present invention for fluorescence detection of lipid membranes, cells were fluorescently labeled with an effective amount of lipophilic, functionalized nanocrystals. In this illustrative example, the functionalized nanocrystals comprised CdSe/ZnS, mercaptocarboxylic acid-capped, lysine-coated nanocrystals of a size that corresponds to a peak emission wavelength of 613 nm (hence, fluorescing a red color when excited). In this example, a human T lymphocyte cell line, Jurkat cells, was used. The Jurkat cells were grown in suspension using suitable culture conditions and medium (RPMI 1640). The cultured cells were then harvested by centrifugation (800×g rpm for 10 minutes). The cell pellet was resuspended, and the cells washed, in a buffer (PBS minus Ca++ and Mg++). After the cells were washed a final time, the washed cells were resuspended in 4 ml of buffer. The cells were checked for viability using trypan blue. One ml containing about $4\times10^6$ cells was slowly added to 3 ml of 70% ethanol with gentle agitation. The mixture was then incubated for a minimum of 30 minutes on ice (alternatively, for up to 48 hours at 4° C.). After the incubation, the cells were harvested by centrifugation. The cells in the pellet were then washed two times with a staining buffer (e.g., PBS containing 3% fetal bovine serum, and 0.1% sodium azide). The cells of the final pellet were resuspended in 1 ml of staining buffer to a final concentration of $4\times10^6$ cells/ml. An aliquot containing $1\times10^6$ cells was added to a microcentrifuge tube, the tube was centrifuged, and the supernatant was removed. The cells in the pellet were resuspended in 100 $\mu$l of buffer containing approximately $1\times10^{14}$ lipophilic, functionalized nanocrystals. The mixture was incubated on ice for 10 minutes. 800 $\mu$l of staining buffer was added to the mixture, the mixture was agitated by vortexing, and the tube was then centrifuged at 1400×g for 6 minutes. The supernatant was removed from the tube, and the cells in the pellet were resuspended in 800 $\mu$l of staining buffer. The cells were again pelleted by centrifugation, and the cells in the pellet were resuspended in 300 $\mu$l of staining buffer. An aliquot of the labeled cells was dropped onto a microscope slide, and coverslipped. The slide was then examined using a reflected light fluorescence microscope with an attachment comprising a fluorescence cube (co-pending U.S. patent application Ser. No. 09/419,134) and an excitation light in the spectral range of from about 300 nm to about 400 nm. In that regard, FIG. 1 is a black and white image of a cell wherein the white and gray areas represent the labeled membrane as detected by the red fluorescence emitted by the lipophilic, functionalized nanocrystals used to label cell membranes according to the method of the present invention. Note the fluorescence is localized to the lipid bilayer comprising the cell membrane, thereby allowing detailed visualization of cell membrane morphology by fluorescence analysis. Thus, provided are lipid membranes labeled by incorporation of lipophilic, functionalized nanocrystals into the membrane structure; and more particularly, provided are cell membranes labeled by incorporation of lipophilic functionalized nanocrystals into the membrane structure.

EXAMPLE 4

In another illustrative embodiment of a method according to the present invention for fluorescence detection of lipid membranes, a substrate comprising tissue comprised of multiple populations of cells is fluorescently labeled with an effective amount of lipophilic, functionalized nanocrystals. In this illustrative example, the functionalized nanocrystals comprised CdSe/ZnS, mercaptocarboxylic acid-capped, lysine-coated nanocrystals of a size that corresponds to a peak emission wavelength of 613 nm (hence, fluorescing a red color when excited). In this example, the lipophilic, functionalized nanocrystals were used in a histological analysis for distinguishing normal tissue from diseased tissue. More particularly, to illustrate this application of the method according to the present invention, normal colonic mucosal tissue and malignant colonic mucosal tissue were each labeled with lipophilic, functionalized nanocrystals. As will be apparent to one skilled in the art, care should be exercised in selecting a method of tissue preparation and labeling which sufficiently preserves the lipid structure and fluidity of the cell membranes for labeling. The tissue used was a clinical colon tumor biopsy which contained portions comprising malignant colonic tissue and portions comprising normal colonic tissue. The tissue was first processed by fixation and paraffin embedding used standard methods known in the art. Briefly, the tissue was first fixed in a 10% buffered formalin, followed by successive treatments with 75% ethanol, three changes of 100% ethanol, three changes of xylene, and three changes in melted paraffin (at 60° C.). A block of paraffin-embedded tissue was made by placing the tissue in a mold with melted paraffin, and allowing the mixture to cool and harden. Tissue sections were then prepared by cutting 5 μm sections and mounting the sections onto treated microscope slides.

Figure 2A:
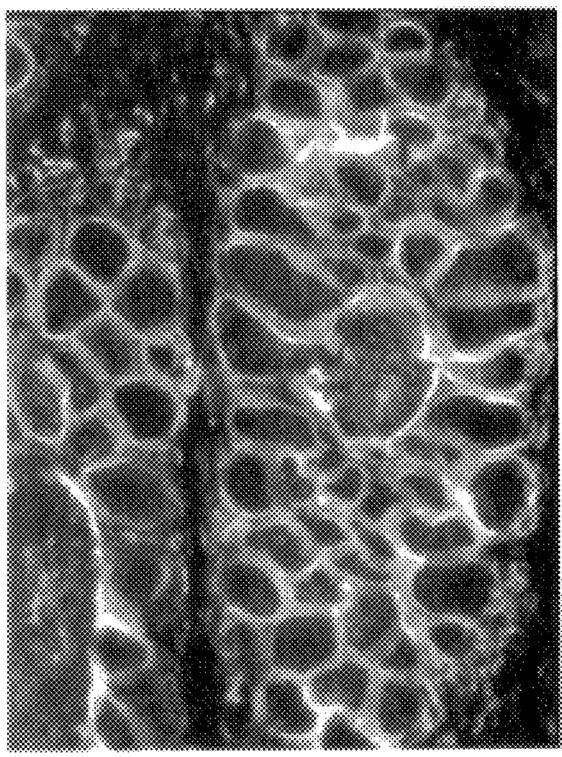
FIG. 2A a black and white representation of a photographic image showing cell membranes of normal colonic mucosa labeled with an effective amount of lipophilic, functionalized nanocrystals.
Figure 2B:
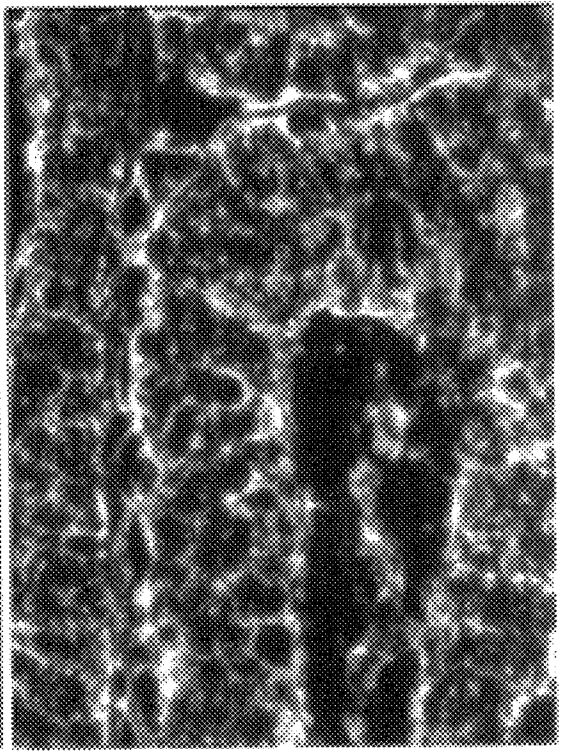
FIG. 2B a black and white representation of a photographic image showing cell membranes of malignant colonic mucosa labeled with an effective amount of lipophilic, functionalized nanocrystals.

Before the labeling process, the mounted tissue sections were treated with an antigen retrieval process using standard methods known in the art. Briefly, the mounted tissue sections were de-paraffinized by short incubations in each of three baths of xylene; and were rehydrated by short incubations in a series of ethanol solutions comprising 100% ethanol, 75% ethanol, 50% ethanol, and 10% ethanol. The mounted tissue sections were then washed in PBS, added to a coplin jar containing a heated antigen retrieval solution (for this particular commercially available solution, 95° C. to 99° C.), and incubated for 20 minutes. The mounted tissue sections were the removed from the jar, allowed to cool, and washed with PBS. The lipophilic, functionalized nanocrystals were added (100 μl of buffer containing approximately $1\times10^{14}$ lipophilic, functionalized nanocrystals) to the tissue sections, and the sections were then incubated for 1 hour. The tissue sections were then washed with PBS, dehydrated by a short incubation in a series of ethanol solutions (50%, 75%, and 100%, respectively), incubated in xylene for 10 minutes, and the dried. The processed tissue sections were then cover-slipped for analysis on a fluorescent microscope using essentially the detection system described in more detail in Example 3 herein. In that regard, FIG. 2A is a black and white image, with the white and light gray areas representing the labeled membranes as detected by red fluorescence emitted by the excited lipophilic, functionalized nanocrystals labeling cell membranes of normal tissue (normal colonic tissue) using the method according to the present invention; whereas FIG. 2B is a black and white image, with the light gray areas representing labeled membranes as detected by red fluorescence emitted by the excited lipophilic, functionalized nanocrystals labeling cell membranes of diseased tissue (malignant colonic tissue) using the method according to the present invention. Note the fluorescence is localized to the lipid bilayer comprising the cell membranes, thereby allowing detailed visualization of cell membrane morphology by fluorescence analysis. In that regard, the labeled cell membranes of normal mucosa, as illustrated in FIG. 2A, show organized membrane structures and morphology characteristic of normal colon tissue. In contrast, as illustrated in FIG. 2B, the labeled cell membranes of the malignant mucosal tissue shows disorganized membrane limits characteristic of malignant colonic tissue, and may further exhibit a relative lesser overall intensity of staining. Thus, as evident from a comparison of FIGS. 2A and 2B, the lipophilic, functionalized nanocrystals may be used in a method for distinguishing diseased tissue from normal tissue, and may be used in a method for distinguishing between different cell populations in a sample comprising multiple cell populations (e.g., whether the sample comprises tissue or a sample of individuals cells), by a parameter of labeled cell membranes selected from the group consisting of cell membrane morphology, intensity of fluorescence emission, pattern of fluorescence labeling, and a combination thereof. FIGS. 2A and 2B also illustrate lipid membranes labeled by incorporation of lipophilic functionalized nanocrystals into the membrane structure; and more particularly, provided are cell membranes labeled by incorporation of lipophilic functionalized nanocrystals into the membrane structure.

It will be apparent to one skilled in the art from the descriptions herein that the lipophilic, functionalized nanocrystals may be used in conjunction with other reagents in an analysis for a substrate (individual cells, cells in a tissue, or liposomes) for multiple components using an appropriate detection means. For example, in addition to labeling the cell membranes of a tissue section, the tissue section may be also stained with one or more additional fluorescent labels targeted to one or more cell components other than the lipid membrane. For example, the above-described tissue section from a clinical colon biopsy (or individual cells of a sample comprised of multiple populations of cells) may be have their cell membranes labeled with the lipophilic, functionalized nanocrystals, and in conjunction, contacted with one or fluorescence detection reagents. A fluorescence detection reagent may comprise an affinity ligand (antibody, lectin, and the like) which has operably linked thereto a fluorescent label (fluorochrome, fluorescent dye, functionalized semiconductor nanocrystal, and the like). In continuing with this example, the tissue section may be reacted and labeled with an effective amount of a fluorescent labeled (e.g., fluorescein labeled)-antibody against a cell surface antigen commonly found on adenocarcinomas (e.g., sTn, or BER-EP4) and not typically found on normal colon tissue, in furthering the distinction between normal tissue and malignant tissue by fluorescence analysis. It will also be apparent to one skilled in the art from the descriptions herein that liposomes may be fluorescently labeled with the lipophilic, functionalized nanocrystals using methods similar to those described herein for labeling individual cells, and further comprising detecting the labeled liposomes.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed:

1. A method for fluorescence labeling of lipid membranes, the method comprising contacting the lipid membranes with an effective amount of lipophilic, functionalized nanocrystals, wherein the functionalized nanocrystals become incorporated into the lipid membranes in labeling the lipid membranes.

2. The method according to claim 1, wherein the lipid membranes comprise individual cells.

3. The method according to claim 1, wherein the lipid membranes comprise a tissue comprised of multiple populations of cells.

4. The method according to claim 1, wherein the lipid membranes comprise liposomes.

5. A method for fluorescence detection of lipid membranes, the method comprising the steps of:

(a) contacting the lipid membranes with an effective amount of lipophilic, functionalized nanocrystals, wherein the functionalized nanocrystals become incorporated into the lipid membranes in labeling the lipid membranes;

(b) exposing the labeled lipid membranes to an excitation light source suitable for exciting the functionalized nanocrystals to emit a fluorescence emission; and (a) detecting the fluorescence emission emitted by the excited functionalized nanocrystals.

6. The method according to claim 5, further comprising mixing the functionalized nanocrystals with a physiologically acceptable carrier prior to contacting the functionalized nanocrystals with the lipid membranes.

7. The method according to claim 5, wherein the excitation light source comprises a spectrum in the range of from about 300 nm to about 400 nm.

8. The method according to claim 5, wherein the fluorescence emission emitted by the excited functionalized nanocrystals is in a spectral range of from about 400 nm to about 750 nm.

9. The method according to claim 5, wherein detecting the fluorescence emission comprises use of one or more of a photodetector, a filter, a CCD camera, a fluorescence microscope, an endoscopic imaging system, an endoscopic fluorescence imaging microscope, a fiber optic fluorescence imaging microscope, a fluorescence cube, and a computer.

10. The method according to claim 5, further comprising quantitating the amount of labeled lipid membranes detected by measuring the intensity of fluorescence emission.

11. The method according to claim 5, wherein the lipid membranes comprise individual cells.

12. The method according to claim 5, wherein the lipid membranes comprise a tissue comprised of multiple populations of cells.

13. The method according to claim 5, wherein the lipid membranes comprise liposomes.

14. The method according to claim 12, further comprising distinguishing diseased tissue from normal tissue by a parameter of labeled cell membranes selected from the group consisting of cell membrane morphology, intensity of fluorescence emission, pattern of fluorescence labeling, and a combination thereof.

15. The method according to claim 12, further comprising distinguishing between different cell populations in a sample by a parameter of labeled cell membranes selected from the group consisting of cell membrane morphology, intensity of fluorescence emission, pattern of fluorescence labeling, and a combination thereof.

16. The method according to claim 11, further comprising distinguishing between different cell populations by a parameter of labeled cell membranes selected from the group consisting of cell membrane morphology, intensity of fluorescence emission, pattern of fluorescence labeling, and a combination thereof.

17. Lipid membranes labeled with lipophilic, functionalized nanocrystals.

18. The lipid membranes according to claim 17, wherein functionalized nanocrystals are incorporated into the structure of the membranes.

19. The lipid membranes according to claim 17, wherein the lipid membranes comprise individual cells.

20. The lipid membranes according to claim 17, wherein the lipid membranes comprise a tissue comprised of multiple populations of cells.

21. The lipid membranes according to claim 17, wherein the lipid membranes comprise liposomes.

* * * * *